US008802424B2

(12) United States Patent
Luong et al.

(10) Patent No.: US 8,802,424 B2
(45) Date of Patent: Aug. 12, 2014

(54) METHODS AND SYSTEMS FOR ANALYSIS OF FLUORESCENT REACTIONS WITH MODULATED EXCITATION

(75) Inventors: Khai Luong, Oakland, CA (US); Paul Lundquist, San Jose, CA (US); Ravi Dalal, Menlo Park, CA (US); John Lyle, Redwood Shores, CA (US); Stephen Turner, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 929 days.

(21) Appl. No.: 12/351,173

(22) Filed: Jan. 9, 2009

(65) Prior Publication Data

US 2009/0181396 A1    Jul. 16, 2009

Related U.S. Application Data

(60) Provisional application No. 61/010,639, filed on Jan. 10, 2008.

(51) Int. Cl.
    C12M 1/00    (2006.01)
    C12Q 1/68    (2006.01)
    C12M 1/34    (2006.01)
    G01N 21/64   (2006.01)
    G01N 1/00    (2006.01)

(52) U.S. Cl.
    CPC .................................... *C12M 1/34* (2013.01)
    USPC ... 435/283.1; 435/6.1; 435/287.2; 422/82.08; 436/176

(58) Field of Classification Search
    CPC ..... G01N 21/6428; G01N 21/75; C12Q 1/68; C12M 1/34
    USPC .................. 435/6.1, 283.1, 287.2; 422/82.08; 436/172
    See application file for complete search history.

(56) References Cited

U.S. PATENT DOCUMENTS

| | | | |
|---|---|---|---|
| 3,971,951 A | 7/1976 | Rikukawa et al. | |
| 5,313,264 A | 5/1994 | Ivarsson et al. | |
| 5,547,839 A | 8/1996 | Dower | |
| 5,591,981 A * | 1/1997 | Heffelfinger et al. | 250/458.1 |
| 5,674,698 A * | 10/1997 | Zarling et al. | 435/7.92 |
| 5,821,058 A | 10/1998 | Smith | |
| 6,038,041 A | 3/2000 | Poon et al. | |
| 6,210,896 B1 | 4/2001 | Chan | |
| 6,245,507 B1 | 6/2001 | Bogdanov | |
| 6,255,083 B1 | 7/2001 | Williams | |
| 6,363,269 B1 * | 3/2002 | Hanna et al. | 600/322 |
| 6,787,308 B2 | 9/2004 | Balasubramanian | |
| 7,023,544 B2 | 4/2006 | Cunningham et al. | |
| 7,056,661 B2 | 6/2006 | Korlach et al. | |
| 7,456,954 B2 | 11/2008 | Weiss | |
| 7,630,073 B2 * | 12/2009 | Lundquist et al. | 356/317 |
| 7,805,081 B2 * | 9/2010 | Lundquist et al. | 398/140 |
| 2003/0058440 A1 | 3/2003 | Scott et al. | |
| 2003/0096253 A1 | 5/2003 | Nelson | |
| 2003/0190647 A1 | 10/2003 | Odera | |
| 2003/0215862 A1 | 11/2003 | Parce | |
| 2004/0048300 A1 | 3/2004 | Sood | |
| 2004/0152119 A1 | 8/2004 | Sood | |
| 2004/0224319 A1 | 11/2004 | Sood | |
| 2005/0247866 A1 * | 11/2005 | Plewa et al. | 250/251 |
| 2006/0061755 A1 * | 3/2006 | Turner et al. | 356/38 |
| 2006/0176917 A1 * | 8/2006 | Grek et al. | 372/29.02 |
| 2007/0161017 A1 | 7/2007 | Eid | |
| 2007/0206187 A1 | 9/2007 | Lundquist | |
| 2008/0212960 A1 | 9/2008 | Lundquist | |
| 2008/0226307 A1 | 9/2008 | Lundquist | |
| 2008/0277595 A1 | 11/2008 | Lundquist | |
| 2009/0042179 A1 * | 2/2009 | Peltie et al. | 435/4 |
| 2010/0167413 A1 * | 7/2010 | Lundquist et al. | 436/172 |

FOREIGN PATENT DOCUMENTS

| | | |
|---|---|---|
| WO | WO 91/06678 | 5/1991 |
| WO | WO 96/27025 | 9/1996 |
| WO | WO 99/05315 | 2/1999 |
| WO | WO 2005/080945 | 9/2005 |

OTHER PUBLICATIONS

Vereb et al, Temporally and spatially resolved imaging microscopy of lanthanide chelates, 1996, Biophysical Journal, 74, 2210-2222.*
Musiani et al, In situ detection of cytomegalovirus DNA in biopsies of AIDS patients using a hybrido-immunocytochemical assay, 1990, Histochemistry, 94, 21-25.*
International Search Report and Written Opinion dated May 28, 2009 for related case PCT/US2009/000146.
International Preliminary Report on Patentability dated Jul. 22, 2010 or related case PCT/US2009/00014.
Eid et al., (Jan. 2, 2009) Science 323:133-138.
Levene et al., (2003) Science 299 (5607):682-686.
Sanden, Tor, et al., "Monitoring Kinetics of Highly Environment Sensitive States of Fluorescent Molecules by Modulated Excitation and Time-Averaged Fluorescence Intensity Recording," Analytical Chemistry, vol. 79, No. 9, p. 3330-3341 (2007).

* cited by examiner

*Primary Examiner* — Narayan Bhat
(74) *Attorney, Agent, or Firm* — Morgan, Lewis & Bockius LLP

(57)    ABSTRACT

Methods, systems and their components for monitoring fluorescent signals and particularly transient fluorescent signals from reaction mixtures of interest, which methods and systems employ modulated excitation light sources to reduce impacts of excessive illumination on the reaction components or the data obtained therefrom.

20 Claims, 6 Drawing Sheets

METHODS AND SYSTEMS FOR ANALYSIS OF FLUORESCENT REACTIONS WITH MODULATED EXCITATION

CROSS-REFERENCE TO RELATED APPLICATIONS

This application claims the benefit of Provisional U.S. Patent Application No. 61/010,639, filed Jan. 10, 2008, the full disclosure of which is incorporated herein by reference in its entirety for ail purposes.

STATEMENT REGARDING FEDERALLY SPONSORED RESEARCH

Not Applicable.

BACKGROUND OF THE INVENTION

A wide variety of biological and biochemical analyses employ fluorescence detection techniques to measure biological interactions. In particular, reactants in a given biochemical reaction may be provided with or may inherently possess fluorescent or fluorogenic groups that, upon illumination with light of an appropriate excitation wavelength, will emit a characteristic fluorescent signal. Depending upon the nature of the analysis, the changed property of the fluorescent group before, during and/or after a given reaction may provide an indication of the progress of the reaction, providing a readily monitorable signal associated with that progress. For example, the localization of a fluorescently labeled probe on a position of a solid support bound compound provides an indication of the affinity of the compound for the probe, e.g., as in the case of oligonucleotide arrays. Alternatively, shifts in the electrokinetic mobility of the fluorescent species may provide an indication of a change in the charge of the fluorescent group, e.g., arising from phosphorylation, cleavage, association with oilier charged species, or the like. In still other systems, immobilization of fluorescent monomers by support bound synthesis complexes may provide an indication of the incorporation of such monomers into polymeric species, by the complexes, e.g., polymerase/template/primer complexes.

With increasingly complex and demanding analytical processes comes a need for sensitive and flexible detection systems. The present invention provides such systems, their constituent components and methods for using them.

BRIEF SUMMARY OF THE INVENTION

Technologies related to analysis of biological information have advanced rapidly over the past decade. In particular, with the improved ability to characterize genetic sequence information, identify protein structure, elucidate biological pathways, and manipulate any or all of these, has come the need for improved abilities to monitor these processes and interpret the results of that analysis.

The present invention generally provides systems for analysis of fluorescent materials, that comprise a reaction region for containing a fluorescent reaction mixture, an excitation light source, a detector, and an optical train for directing excitation light from the excitation light source to the reaction region and collecting fluorescent signals from the reaction region and directing the fluorescent signals to the detector. In accordance with certain aspects, at least one of the optical train and the excitation light source is configured to provide a modulated beam of excitation light to the reaction region.

Other systems of the invention comprise a reaction region containing at least first and second fluorescent reactants, where the first and second fluorescent reactants are excited by first and second excitation beams having different wavelength spectra, respectively, and where simultaneous excitation of the first and. second fluorescent reactants further excites at least one of the first and second fluorescent reactants to a triplet state. The systems also comprise a source of first and second excitation beams, a detector, and an optical train for directing the first and second excitation beams to the reaction region, modulating at least one of the first and second excitation beams, and directing fluorescent signals emitted by the first and second fluorescent reactants to the detector.

Still other systems of the invention comprise a reaction region containing a reaction mixture that comprises at least first and second fluorescent reactants, the first and second fluorescent reactants having at least first and second distinct excitation spectra. First and second excitation light sources are provided that are configured to provide excitation light at the first and second excitation spectra, respectively. An optical train is also provided that directs excitation light from the first and second excitation light sources to the reaction region, and modulates the excitation beams from at least one of the first and second excitation light sources at a frequency of at least 50 Hz.

The invention also provides methods for detecting fluorescent reactants. In a first aspect, the methods comprise providing a reaction mixture containing at least first and second fluorescent reactants, the first and second fluorescent reactants being excited by first and second excitation beams having different wavelength spectra, respectively, and wherein simultaneous excitation of the first and second fluorescent reactants further excites at least one of the first and second fluorescent reactants to a triplet state. The methods further comprise directing the first and second excitation beams at the reaction region, modulating at least one of the first and second excitation beams directed at the reaction region, and detecting fluorescent signals emitted from the first and second fluorescent reactants.

In related aspects, the methods of the invention comprise detecting fluorescent reactants from a reaction mixture that comprises at least first and second fluorescent reactants that are excited by excitation beams of different wavelengths, where simultaneous excitation of the first and second fluorescent reactants excites at least one of the first and second fluorescent reactants to a triplet state. In these methods, at least one of a first and second excitation beam directed at the reaction mixture is modulated.

In another aspect, the invention provides methods of analyzing fluorescent materials that comprise providing a reaction mixture comprising one or more of fluorescent reactants or products, directing a modulated excitation illumination beam at the reaction mixture, and detecting fluorescent signals produced by the reaction mixture in response to the modulated excitation beam.

DETAILED DESCRIPTION OF THE INVENTION

I. Fluorescence Detection

Figure 1:
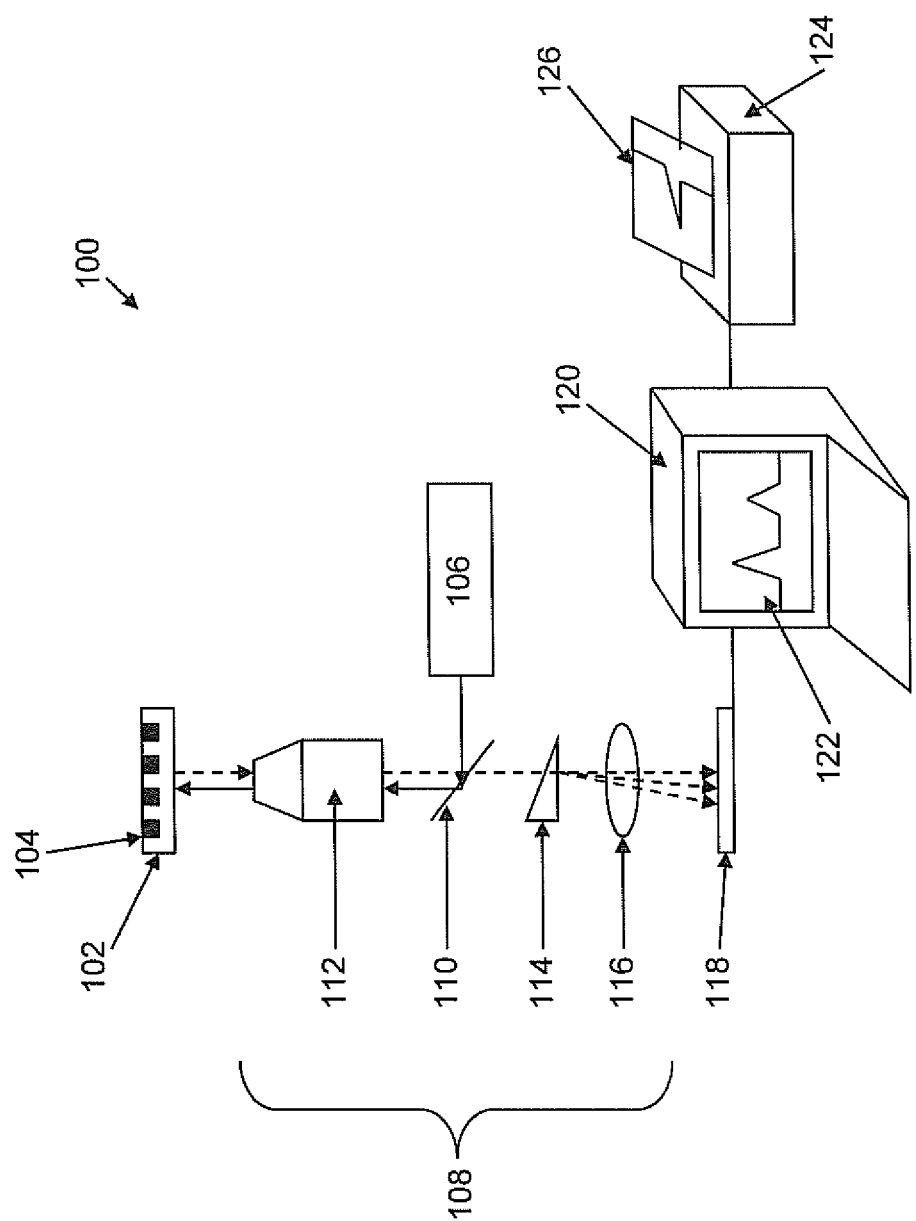
FIG. 1 schematically illustrates an exemplary fluorescence detection system.

Analysis of fluorescent reactants or reaction products by directing excitation illumination at these materials and detecting the consequent fluorescent emissions, has become a standard method for analyzing chemical, biochemical and biological processes. Unfortunately, however, in many fluorescence analysis systems, excessive or continuous illumination of the reactants to be observed can yield detrimental effects on those reactants. For example, excessive illumination can give rise to heating effects which can impact the reactions being observed. Additionally, fluorescent species subjected to constant illumination may photobleach to the point of having reduced or lost fluorescence. Fluorescent compounds that are excited may also contribute to detrimental impacts on other reaction components through generation of harmful chemical species, e.g., oxygen radicals.

In a particular exemplary system, individual DNA polymerase/template/primer complexes, immobilized on a solid support, are illuminated with excitation light while they incorporate fluorescently labeled nucleotide analogs. Characteristic fluorescent signals emanating from these individual complexes indicate whether a given nucleotide is incorporated by the complex. In some methods, labeled nucleotides are actually incorporated while still bearing the fluorescent label group. Unincorporated labeled nucleotides are then washed away from the immobilized complex and the complex is illuminated and fluorescent signals monitored to determine the presence of an incorporated fluorescent nucleotide. The fluorescent label is then removed from the incorporated nucleotide and washed from the system. A second nucleotide is contacted with the complex and its incorporation or lack thereof, is monitored in the same fashion. In some aspects, these systems employ a single type of nucleotide in each step, requiring a cycled process of interrogating the complex with each of the four types of nucleotides. This permits only one type of analog to be added in each step. In related methods, nucleotide analogs that employ terminator groups, e.g., that prevent additional nucleotides from being added, are used. In these methods, all four different types of nucleotides may be added in a single step. However, because each nucleotide includes a terminator group, only one nucleotide will be added. In order to perform iterative incorporation steps, then, both the label group and the terminator group must be removed and washed from the complex prior to detection.

In still another and more preferred aspect, a polymerase/template/primer complex is provided within a confined illumination volume that localizes the illumination to the area including a single complex and not much more. As labeled nucleotides are incorporated by the complex, they are retained within the illumination volume for periods longer than the average diffusion time of unincorporated nucleotides, thus giving a characteristic optical signal associated with that incorporation. Further, by employing nucleotides that bear the fluorescent label on the beta, gamma or more distal phosphate group of a nucleoside polyphosphate, the label group is automatically cleaved during incorporation. The result is that following the characteristic incorporation fluorescent signal, the label group is released to behave more like randomly diffusing nucleotides. As a further result, one is able to monitor nucleotide incorporations in real time as they occur. By labeling each type of nucleotide (e.g. A, G, C and T) with a spectrally distinguishable fluorescent label or dye and monitoring the reaction for the different fluorescent signals, one can not only identify an incorporation event, but also identify the type of nucleotide incorporated.

As noted above, the illumination based detection systems described herein, e.g., fluorescence detection systems, can give rise to certain adverse effects. For example, as noted above, illumination induced heating of reactions can impact the progress and longevity of reactions. For example, and as noted above, illumination induced heating of reaction mixtures can substantially alter reaction kinetics, and even damage reaction components to the point of substantially impacting the analysis of the reaction. In particular, fluorescence detection systems typically employ highly concentrated laser illumination in order to provide the greatest level of energy to excite the maximum level of fluorescence. Directing such large amounts of energy at relatively small reaction volumes can also result in substantial heating of the reaction mixture. Such heating will directly impact reaction kinetics, move reactions out of optimal temperature ranges for biochemicals, and potentially damage reaction components, e.g., denaturing proteins, preventing annealing of nucleic acids, or otherwise damaging sensitive reagents.

Fluorescent compounds themselves may also be negatively impacted by excessive illumination. In particular, most organic fluorescent dyes demonstrate reduced fluorescence over prolonged illumination. Such photobleaching can substantially reduce the amount of fluorescence derivable from a fluorescent reaction mixture.

In addition, excessive illumination of biological materials in the presence of optically active chemicals, such as fluorescent dyes or fluorophores. can result in additional adverse impacts (See, e.g., Published U.S. patent application No. 2007-0161017, the full disclosure of which is incorporated herein by reference in its entirely for all purposes). One example of such detrimental impacts includes the decrease in enzyme activity in the presence of excited fluorescent substrates, also termed "photodamage". By way of example, and without being bound to a particular theory of operation, in the context of certain methods of observation of polymerase mediated nucleic acid synthesis, a fluorophore coupled to a nucleotide analog is excited by exposure to electromagnetic radiation at an excitation wavelength, which exists while the nucleotide is proximal to or within the active site of the polymerase or other enzyme. This fluorophore can transition into a triplet state. Subsequent relaxation of the triplet state fluorophore can then lead to generation of reactive oxygen species, which can, in turn, damage one or both of the fluorophore or the polymerase. It is also believed that multiphoton processes, e.g., photon exposure to the excited fluorophore, can lead to additional damaging pathways. In particular, where an excited fluorophore absorbs a second photon from a shorter wavelength, or bluer, excitation source than its nominal absorption peak, it can transition to a higher excitation stale where it can then transition to damaging species, like radicals or exiplexes. In highly illuminated reaction systems and systems that employ multi-wave length illumination systems, the increased influx of photons to the sample results in higher levels of these multiphoton processes. Further, such photodamage mechanisms may also be highly dependent upon the nature of the fluorophore used, e.g., certain dyes emitting at a particular wavelength may cause greater amounts of photodamage than others.

Photodamage of inorganic compounds is known to be highly non-linear. Restated, photodamage is generally extremely low or non-existent up to a particular threshold level, beyond which catastrophic damage occurs. This same result is also believed to be evident in enzyme based systems, such as DNA polymerases, where enzyme activity under photodamaging conditions, would remain constant up to a certain level of illumination, but beyond which the enzyme activity would drop precipitously.

In addition to the impacts of illumination intensity of reaction components or conditions, excessive illumination energy can also have negative impacts from a system standpoint, as well. In particular, in fluorescence based systems, some fraction of signal noise results directly from the illumination light being used in the system. Key contributors to this noise are reflected, scattered or otherwise misdirected excitation illumination, and autofluorescence of the various components of the system, including optical components, reaction vessel substrates, and reaction constituents. All of these noise levels are a function of the level of excitation illumination being pumped, into the system. For a discussion of autofluorescence and strategies for its mitigation, see, e.g., U.S. Patent Application Nos. 60/928,617, filed May 10, 2007, Ser. No. 11/901,273, filed Sep. 14, 2007, the full disclosures of which are incorporated herein by reference in their entirety for all purposes.

As will be appreciated, in systems that utilize multi-wavelength illumination, e.g., using multiple simultaneous excitation sources, e.g., lasers, having different spectra, the illumination intensity can be quite high, resulting from two, three, four or more excitation beams being directed through the system and at the reaction region, at any given time. As a result such multi-wavelength systems run an even greater risk of the illumination induced adverse effects described above, including, in particular, multiphoton effects on certain fluorophores.

An exemplary fluorescence detection system is schematically illustrated in FIG. 1. As shown, the overall system 100 includes one or more excitation illumination sources, i.e., laser 106. The excitation light from laser 106 is directed to a reaction region, e.g., reaction region or well 104 on substrate 102, by the optical train 108. Although optical trains may vary depending upon the desired application, as shown, the excitation beam from laser 106 is directed at and reflected by a dichroic mirror 110. and passed into objective lens 112, which focuses the excitation beam onto the reaction region/well 104 of substrate 102. Fluorescent signals emitted from the reaction regions in response to the excitation beam are then collected by objective lens 112, and, by virtue of their shifted wavelength relative to the excitation beam, are transmitted through dichroic mirror 110. The fluorescent signal, is then focused by focusing lens 116 onto a detector 118, which registers the incident signal thereon. As shown, the fluorescent signal may also be subjected to spectral separation to separate out spectrally different signal components that emanate from different reactions or different events in the same reaction. As shown, spectral separation is accomplished by passing the fluorescent signal through a dispersive optical element, such as wedge prism 114 to direct spectrally different signals or signal components to different regions of the detector 118.

Signals received by the detector 118 are then recorded and processed by a processor such as computer 120, and displayed in a convenient user friendly format, e.g., display 122 or printout 126 from printer 124.

II. Excitation Beam Modulation

The present invention is directed to systems and methods for the optical analysis of materials and reactions, such as is described with reference to FIG. 1. but using modulated illumination energy in order to minimize adverse impacts of such illumination on the observed system. In particular, the invention employs optical systems that include illumination sources or paths that result in a modulated illumination beam or beams reaching the desired observation region of the system, e.g., containing the reaction of interest. By modulating the illumination beam, one can separate excitation wavelengths that may cause problems when used simultaneously, significantly reduce the amount of illumination energy that is incident upon the reaction being observed, while still maintaining sufficient illumination to excite fluorescent species and observe the reaction, and provide an excitation profile that may be synchronized with detection to facilitate interpretation of emission signals. All of these aspects provide substantial advantages to fluorescent detection systems.

Provision of a modulated illumination beam at the point of desired illumination, also referred to herein as "beam chopping", may be accomplished through a number of mechanisms. For example, the source of illumination energy may be configured to directly provide a modulated illumination beam, e.g., providing a modulated beam at a desired frequency, to effect a modulated beam at the reaction region. Modulated or modulatable light sources include, e.g., switched lasers, pulsed lasers, direct diode lasers, laser diodes or other solid, state light sources that can be modulated through modulation of applied current, electro-acoustic modulated lasers, and the like.

Alternatively or additionally, the illumination path of an overall optical system which conveys illumination radiation from its source to the point of desired illumination, may include optical components that modulate an otherwise constant beam. Such components may include mechanical modulation mechanisms, such as simple chopping wheels, high frequency shutters, or other mechanical components, such as oscillating or rotating mirrors, baffles, or other components. While effective for many applications, such mechanical mechanisms are generally less preferred for highly sensitive optical systems, as the motion caused by mechanical modulation may impact the precision of light direction, and the like.

Accordingly, solid-state modulation systems are used in preferred implementations of die invention. Such solid state systems include, for example, LCD based filters or apertures, acousto-optical modulators, electro-optical modulators, digital light processors (DLP), and the like, that can be operated at relatively high frequencies to effect beam chopping. In preferred aspects, electronic systems are employed, as they may be readily synchronized with other electronic systems or subsystems employed with the invention, e.g., detector capture frequency, such as the frame capture frequencies of CCD cameras, and the like.

Figure 2:
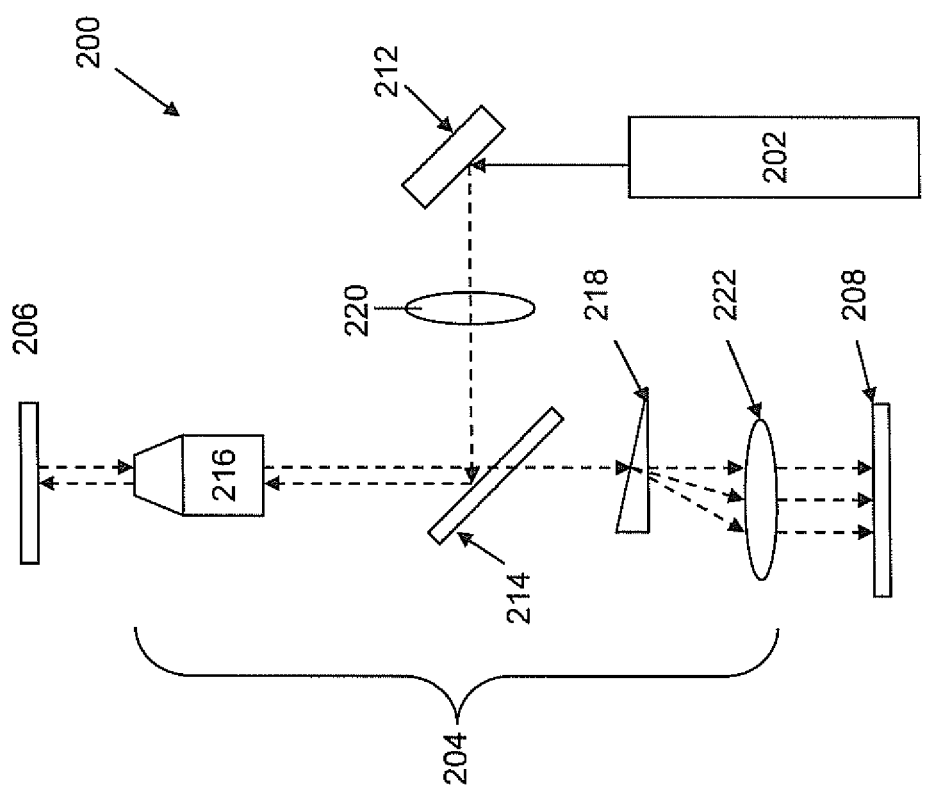
FIG. 2 schematically illustrates a fluorescence detection system employing modulated excitation.

A schematic illustration of an optical system employing a modulated illumination beam is shown in FIG. 2. As shown, an overall optical system 200 includes an excitation illumination source 202, and an optical train 204 for conveying excitation illumination to a reaction region, vessel or the like, e.g., substrate 206. Fluorescent emissions from the reaction region or substrate 206 are then collected through the optical train 204 and directed to a detection system, e.g., a detector array 208. In accordance with the invention, a beam modulation component, e.g., DLP 212, is included within the optical train 204. In operation, excitation illumination (shown as a solid arrow) is directed from excitation source 202, at or through, as the case may be, the beam modulation component, e.g., DLP 212, to produce a modulated beam (shown as the dashed arrow). The modulated beam is then conveyed by the optical train 204 to the reaction region on substrate 206. As shown, in passing through the optical train 204, the modulated beam first is reflected by dichroic mirror 214, which transmits excitation light but is reflective of the fluorescent signals. The modulated beam then passes through objective lens 216 to be focused upon the desired portion(s) of substrate 206. Fluorescent signals emanating from the reaction region (s) on substrate 206 in response to the modulated excitation beam are then collected by and passed through the objective lens 216 and are passed through dichroic 214, and directed to detector 208. Additional optical components are typically included within the optical train in order to adjust the focus of the excitation beam and/or the fluorescent signals, e.g., dispersive optical elements such as prism 218, and lenses 220 and 222, respectively. Additionally, other components, such as cut-off or notch filters, confocal apertures or arrays, mirrors, diffusive optical elements such as gratings or prisms, beam multiplex, or beam shaping optical components, such as lens arrays, holographic optical elements, cylindrical lenses, or the like, may also be included depending upon the desired application (See. e.g., U.S. patent application Ser. No. 11/901,273, filed Sep. 14, 2007, and previously incorporated herein by reference in its entirety for all purposes).

In the case of systems that employ multiple wavelengths in the illumination of a given reaction region, e.g., to observe multiple different fluorescent species, one can cycle each excitation wavelength such that a subset of illumination wavelengths are incident upon the reactants at any given time, and in some cases, only a single beam of a selected excitation wavelength will be incident upon the reactants at a given time. In cases where two, three or four different beams are simultaneously incident upon a reaction region, a system that interleaves such illumination, i.e., resulting in only single beams being incident upon the reaction region. As noted, the separation of different excitation wavelengths incident upon the reaction region can dramatically reduce multi-photon effects on the fluorescent species present.

Further, in cases where excitation illumination intensity of a modulated beam is not required to be increased to make up for shorter duration illumination, excitation beam modulation can result in a reduction of incident illumination energy at any given time, as a result of fewer than all of the excitation beams being directed at the reaction at any given time. The amount of reduction may be controlled to provide for range of different reductions, depending upon the frequency of modulation, e.g., based upon the duty cycle of the chopper or frequency of other types of modulators. By way of example, if one modulates and interleaves two lasers, each supplying the same illumination power, such that they each separately illuminate the reaction, one would achieve at least a 50% reduction in illumination intensity. Likewise, for three or four excitation beams, one could see at least a 67% or 75% reduction, respectively.

Figure 3:
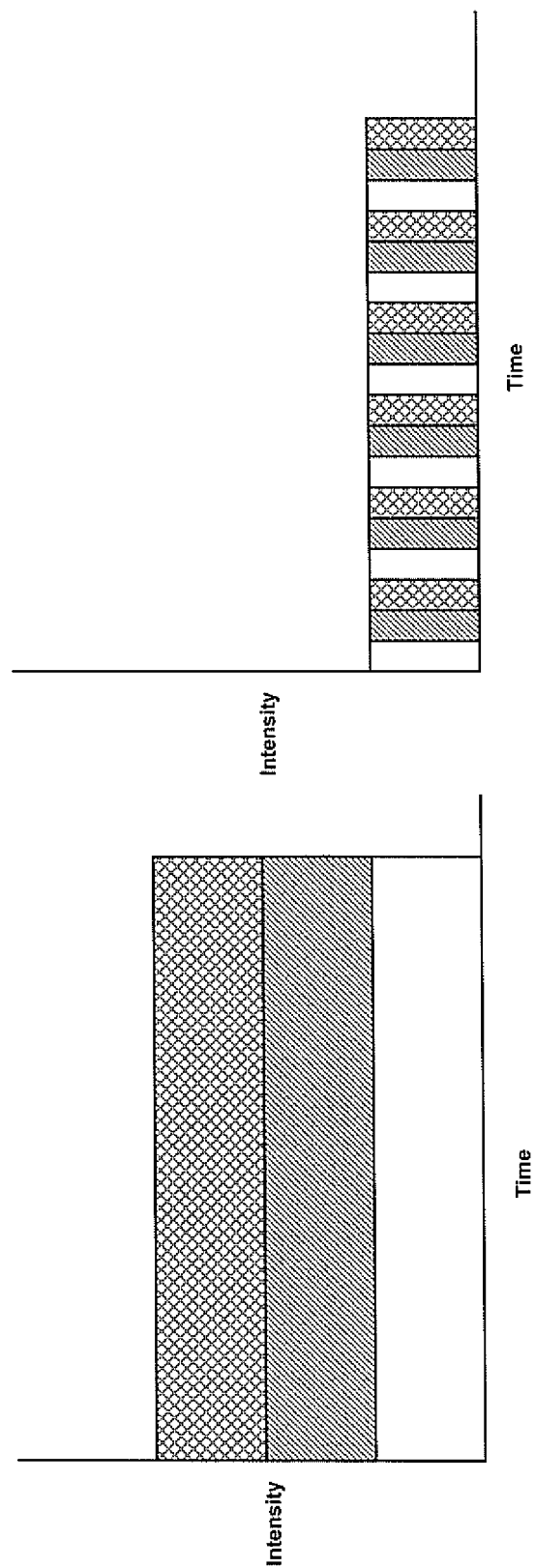
FIG. 3A illustrates a plot of relative illumination intensity incident upon a reaction region as a function of time using constant excitation illumination from multiple sources.
FIG. 3B illustrates a plot of illumination intensity as a function of time using multiple modulated and interleaved excitation sources.

This aspect of the invention is schematically illustrated in FIGS. 3A and 3B. In particular. FIG. 3A shows the cumulative illumination intensity from three light sources (shown as differently shaded bars), e.g., used to excite three or four different fluorescent dyes. FIG. 3B, on the other hand illustrates interleaved, chopped illumination from the three different light sources. As shown, the cumulative energy applied to the reaction region at any given time is a third of that shown in FIG. 3A. As noted elsewhere herein, FIG. 3B shows a system where all applied beams are chopped, although fewer than all of the applied beams may be modulated, depending upon the application.

As noted above, multi-photon processes can have a substantial negative effect on illuminated fluorescent reaction systems, which may be in. addition to or in place of other effects more directly resulting from higher applied radiation (higher applied radiation also provides greater likelihood of multi-photon interactions). In particular, as noted previously, the continued excitation of an already excited fluorescent species may give rise to photo-damaging effects. Notably, some fluorophores, when in an excited state, will absorb light of a shorter, or bluer, wavelength than their nominal excitation wavelength. As noted previously, this can lead to the creation of a transition state for the fluorophore than generates other, potentially damaging species.

Accordingly, by cycling through the different excitation sources, rather than allowing continued exposure to a given excitation wavelength, one can provide the fluorophores the opportunity to relax prior to re-excitation, yielding reduced opportunity for photodamage. Further, in those cases where a particular wavelength or combination of wavelengths is known to suffer ill effects of multi-photon processes, one can adjust the timing of such wavelengths to minimize these effects. By way of example, if two excitation wavelengths in a multi-wavelength system contribute to multi-photon effects of a given fluorophore, then spacing such wavelengths apart in the excitation cycle, e.g., by providing an intervening excitation wavelength between them to give the excited fluorophore sufficient time to return to its relaxed or ground state. The advantages of interleaved excitation in such situations even apply where one has not reduced the average intensity of applied illumination at any given time. For example, in instances where one is seeking to derive maximum emission photons from fluorophores, e.g., in single molecule detection, in using a chopped or modulated excitation beam or beams, it will often be desirable to apply a higher intensity radiation in order to yield the same emission output of the system that one would achieve using a non-modulated beam. For example, if the reaction is only illuminated 25% of the time as a result of beam modulation, one may increase the illumination intensity 4×, in order to yield the same emission output. In such cases, the average illumination intensity over time for the modulated system may approach, equal and/or exceed that of an unmodulated system. However, because separate excitation beams of differing wavelengths are separated, one can avoid certain multi-photon processes, and thus avoid negative impacts of those processes. In particular, where a given fluorophore is excited by a first excitation beam, and in its excited state, absorbs at a wavelength of a second excitation beam, one can separate the first and second excitation beams through interleaved modulation, to allow the first fluorophore to relax prior to the second beam being directed at the reaction. This can result in relatively simple interleaving profiles, such as modulating all but one excitation beam in phase, while the problem excitation beam (at the wavelength absorbed in the multi-photon process described above), is modulated out of phase. Alternatively, more complex modulation and interleaving profiles may be employed, such as modulating all beams out of phase with each other, modulating sub-sets of excitation beams in or out of phase with each other, adjusting the order of excitation beams through interleaving and modulation, and the like.

Figure 6:
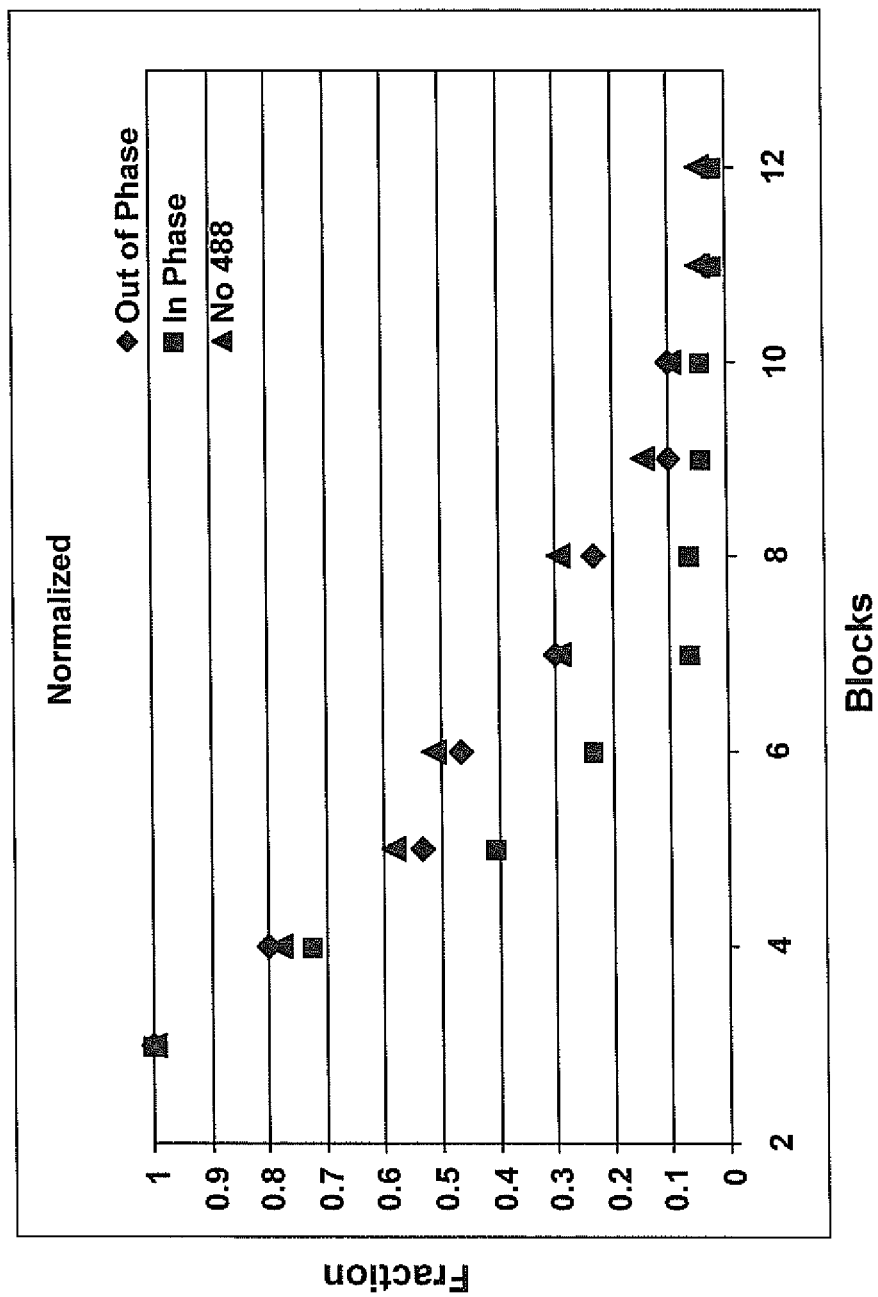
FIG. 6 shows a comparison plot of reaction length for different modulated excitation illumination profiles.

The advantages of interleaving excitation illumination beams in a chopped or modulated process are illustrated in FIG. 6. In particular, a single molecule, real time nucleic acid sequencing process was run where incorporation events were directly monitored under fluorescent excitation illumination, e.g., as described elsewhere herein. In particular, a processive, exonuclease deficient polymerase was immobilized and complexed with template and primer within zero mode waveguides (ZMWs) on a ZMW array, such that individual polymerase molecules (or molecular complexes) were individually optically resolvable. While described in terms of zero mode waveguide confinements, other single molecule arrays are also envisioned for use with the invention, including arrays of molecules provided diluted on the surface of substrates such that individual complexes may be resolved from one another during signaling events, e.g., label incorporation or binding. Such optical resolvability typically requires sufficient spacing between adjacent molecules to allow for the assignment of a given signal to a given location (See, e.g., European Patent No. 1105529 B1, to Balasubramanian et al., which is incorporated herein by reference in its entirety for all purposes).

Primer extension was then carried out using phosphate labeled nucleotide analogs each bearing a different fluorescent group, e.g., having excitation emission maxima of 495/519 nm, 555/565 nm, 578/603 nm and 650/665 nm. The reaction was illuminated using 488 nm, 568 nm and 633 nm lasers.

The template sequence used was a linear template that included registration sequences of known length, termed "blocks". Sequencing of the template would provide a readlength indicated by the number of blocks that were sequenced. FIG. 6 shows a plot of the fraction of all sequence reads that reached a given readlength (measured as blocks of bases) in each of three different illumination patterns: (1) the 488 nm laser modulated in phase with the 568 and 633 lasers (black square); the 488 nm laser modulated out of phase with the 568 and 633 lasers (black diamond); and the 488 nm laser turned, off, with only 568 and 633 illumination (triangle). As evident from FIG. 6, modulating the 488 laser out of phase with the other lasers yields readlength (and by extrapolation, reaction viability) on par with a system in which the 488 nm laser is switched off entirely. Accordingly, separated modulation of illumination (interleaved) can be shown to yield dramatic improvements in reaction survivability under potentially damaging excitation illumination. As will be appreciated a variety of adjustments could be made to chopping frequency and/or patterns, to optimize for a given fluorescent profile of a desired reaction system.

Figure 4:
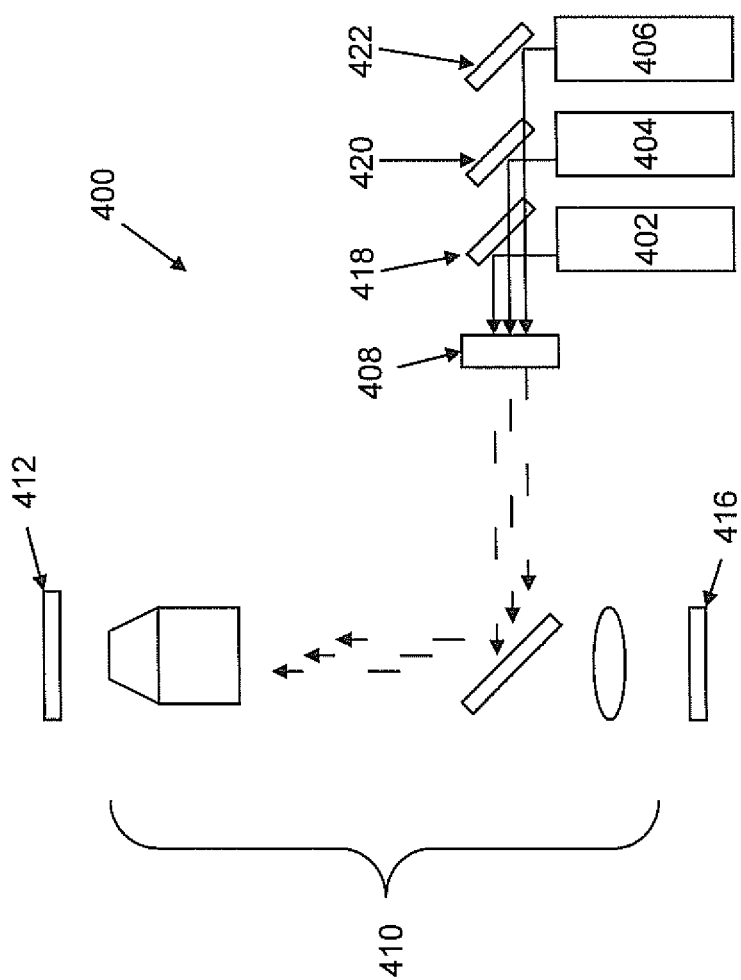
FIG. 4 schematically illustrates a fluorescence detection system employing multiple interleaved excitation light sources.

A schematic illustration of a multiple illumination source system according to the invention is illustrated in FIG. 4. As shown, the system 400 includes multiple excitation light sources, e.g., lasers 402, 404 and 406. Although illustrated having three lasers, such systems may include 2, 3, 4 or more different excitation sources depending upon the desired application of the system, e.g., the type of fluorescent excitation and/or detection desired. By way of example, a system employing three lasers that provide excitation illumination centered around 488 nm, 532 nm and 641 nm respectively, can be employed in exciting four spectrally distinguishable fluorescently labeled reactants, e.g., that excite/emit at 495/519, 555/565, 578/603 and 650/665.

The four different excitation sources are directed at a beam modulation component 408, in the optical train 410. The modulation component may be configured to modulate one, some or all the beams from the different light sources 402-406, depending upon the desired application. For example, in certain preferred aspects, the modulation component will synchronously modulate the various beams in turn, to interleave the different, excitation beams passing into the remainder of the optical train, such that a beam from a single excitation source (or having a set wavelength range) is directed to the reaction region at any given time. This is illustrated as the staggered dashed arrows emanating from the modulation component 408. Each modulated beam is then directed via optical train 410. to the desired reaction region, e.g., on substrate 412. Fluorescent emissions responsive to the modulated excitation beams are then collected by the optical train 410 and directed through focusing lens 414 to detector 416.

Although illustrated as passing all beams through a single modulation component, in some cases, each illumination beam may be passed through a separate modulation component, in order to facilitate arrangement of optical components. As will be appreciated, in preferred aspects, the multiple modulation components will preferably be synchronized to interleave the excitation beams incident upon the substrate, or otherwise provide the desired illumination timing/spacing. With reference to FIG. 4. the single modulation component 408 may be replaced with separate modulation components for each of lasers 402, 404 and 406, e.g., replacing mirrors 418, 420 and 422 with, e.g., individual DLP chips.

In further aspects of the invention, the acquisition rate of the detector, e.g., frame rate in the case of imaging detectors, may be synchronized with the modulated excitation beams, so that excitation and emission correspond with detection windows for the detector. For example, in the case of CCD based detectors, excitation may be timed to correspond with a single image frame or number of frames, so that a given image frame or frames may be directly assigned to a given type of excitation light, facilitating identification of each detected signal, e.g., in a given frame, one can identify a given signal as having been responsive to a given excitation source, and thus assign an identification characteristic to that signal. This is a particularly useful aspect of the invention when applied to the spectroscopic analysis of fluorescent signal pulses from arrayed reaction regions, e.g., performing single molecule, real-time analysis of polymerase mediated, template dependent nucleic acid synthesis, as described below. In particular, exemplary spectroscopic systems employed in analysis of temporally evolving fluorescent signal pulses from arrayed reaction regions are described in, e.g., U.S. patent application Nos. 2007-0206187 and 2007-0036511, the full disclosures of which are incorporated herein by reference in their entirety for all purposes.

The data that is produced from such systems includes spatial data, e.g., data that provides the location of the complex, and thus its identity for the continued or subsequent data acquisition/analysis, as well as the spectral data, e.g., the spectral make-up of the signal component from a given location. In the context of preferred systems, such spectral data is dictated by the use of a dispersive optical element that separates the spectral, components of each, spatially distinct signal. Interpretation of the spectral data typically involves evaluation of a number of different parameters associated with the signal (See. e.g., U.S. patent application No. 60/933,399, filed Jun. 6, 2007, which is incorporated herein by reference in its entirety for all purposes).

By synchronizing the detector with the excitation radiation used, one can elevate the confidence in identification of spectral data by understanding that such data arose only under a given excitation spectrum. Thus, the knowledge that only excitation wavelength X was incident upon the sample region when a given spectral signal occurred, will enhance the confidence that the signal is produced by the fluorophore(s) that emit in response to wavelength X. This provides a powerful metric in spectral identification and its outflow, e.g., base calling in fluorescent sequencing methods. Such synchronized excitation and detection also substantially reduces the amount of background noise, e.g., from reflected excitation illumination, autofluorescence, and the like, that results from the other illumination sources. Also worth noting is that the use of synchronized illumination and detection systems can. to some extent obviate the need for spectral signal separation, where there is sufficient difference between excitation spectra of the various signals. In particular, if only one illumination spectrum excites only one type of signal, e.g., one of the fluorescent dyes, then one can attribute an emission signal to its synchronized excitation event, obviating the need for additional spectral separation to identify the emission spectrum. As will be appreciated, the foregoing advantages are particularly useful in situations where a single excitation line only efficiently excites one or a subset of all of the various fluorophores that are relevant in the reaction of interest.

Figure 5:
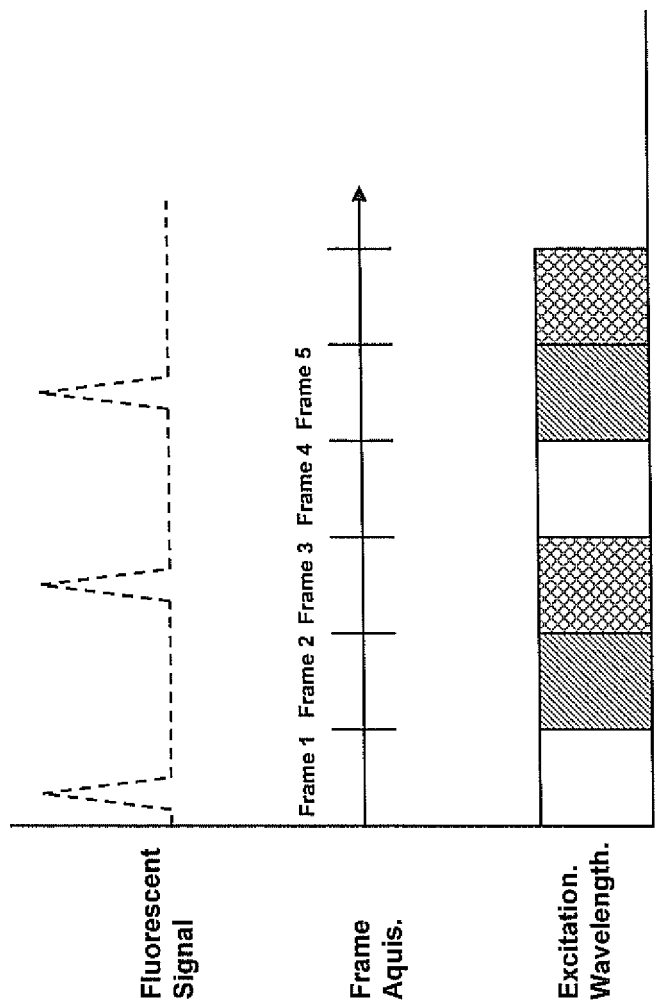
FIG. 5 provides a graphic representation of the inter-relation between interleaved excitation, responsive fluorescent signal generation and detector frame acquisition.

FIG. 5 schematically illustrates the synchronization of the camera or detector frame acquisition with the excitation illumination. In particular, as shown, three different excitation wavelengths are cycled over time, illustrated as wavelength 1 (the unfilled bar), wavelength 2 (the hatched bar) and wavelength 3 (the cross-hatched bar). The signal responsive to excitation illumination, is plotted against the same timeframe (dashed line). The frame acquisition of the detector or camera, is illustrated as a divided arrow, where each tick represents a new image frame. As shown, each image frame is correlated to a single excitation wavelength, and the signals within that frame (indicated as the peaks in the dashed line plot) would have been primarily excited by that wavelength. This information is considered, along with any additional spectral information, e.g., dispersion patterns, etc., as a characteristic in identifying the signal or its source, e.g., the type of nucleotide incorporated in a sequencing analysis.

In accordance with the invention, the frequency of modulation for the excitation beam(s) typically will, be selected and/or configured, such that it does not otherwise interfere with the desired analysis. By way of specific example, where one is monitoring a transient fluorescent signal, e.g., that is associated with a transient reaction event, such as substrate conversion, reactant movement or translocation, or the like, the frequency of modulation must be selected such that one is confident that excitation illumination will be provided to every such transient event. Further, as will be appreciated, in order to provide confidence that one is not detecting an aberrant signal event or noise, the level of "sampling" of a reaction region, through excitation illumination, will preferably be multi-fold over the transient reaction period, e.g., 2×, 4×, 8×, 10× or even greater. In some cases, excessive sampling may also give rise to additional noise levels from the additional illumination, so specific sampling rates may differ within the above ranges, for different applications.

This aspect of the invention is meaningfully illustrated by reference to preferred methods of real-time analysis of polymerase mediated, template dependent nucleic acid synthesis. In particular, such methods typically employ a polymerase/template/primer complex immobilized in an optically confined space to provide a very small zone or volume of illumination. Examples of such confinements include complexes immobilized on the surface of transparent substrates that are illuminated using total internal fluorescence (TIRF) spectroscopy, where evanescent decay of the totally internally reflected illumination results in only a very thin layer of illumination at the surface of the substrate, waveguide array based systems that utilize a similar evanescent decay above optical waveguides that are disposed in planar substrates (See, e.g., U.S. patent application Ser. No. 11/849,157, filed Aug. 31, 2007, the full disclosure of which is incorporated herein by reference in its entirety for all purposes). Alternatively, optical confinement is provided by immobilizing the complexes within zero mode waveguides (ZMWs) disposed through opaque, e.g., metal, cladding layers over transparent substrates (See. U.S. Pat. Nos. 6,917,726, 7,013,054, 7,181,122, 7,292,742 and 7,170,050 and 7,302,146, the full disclosures of which are incorporated herein by reference in their entirety for all purposes). Such ZMWs typically have cross sectional dimensions that range from about 20 nm to about 200 nm. having an illumination depth of from about 10 to about 50 nm, yielding illumination volumes in the range of 10's to 100's of zeptoliters.

In the context of ZMW confined polymerase complexes, it has been determined that fluorescently labeled nucleotides that are being incorporated into a primer extension reaction remain within the illumination volume for a greater amount of time than randomly diffusing molecules. In particular, such incorporated molecules typically demonstrate a retention time within the illumination volume of from about 10 ms to about 100 ms, while randomly diffusing molecules typically remain in the illumination volume for much less time, e.g., on the order of 0.01 ms to about 0.001 ms.

As a first order, therefore, the frequency of modulation for the illumination beam will be selected to provide at least 1× sampling of an incorporation event by a given excitation beam. Thus, for retention times that are about 10 ms. a frequency of greater than 100 Hz would be expected to yield a 1× sampling of any incorporation event, For greater sampling rates, higher frequencies are desirable, e.g., 5× sampling would require a greater than 500 GHz frequency. Of course, advantages may also fie gained by providing a frequency that provides sufficient sampling of incorporation events, while at the same time missing random diffusion events that can contribute to noise levels associated with such random diffusion.

In certain aspects, therefore, where one wishes to reduce noise contribution from randomly diffusing fluorescent species, one will want to select an illumination frequency that provides a sampling rate that is greater than 1, and preferably at least 2, 4, 8, 10 or more, for fluorescent nucleotides that are incorporated, and 1 or preferably less than 1, e.g., 0.5, 0.25, 0.1 or less, for randomly diffusing fluorescent molecules within the illumination volume. Sampling rate is typically calculated, by the equation:

$$S = (T_i)(F)$$

where S is the sampling rate, $T_i$ is the illumination or retention time of the molecule within the illumination volume and F is the modulation frequency of the excitation illumination beam. Thus, a fluorescent molecule that is present in the illumination volume for 20 ms, with a modulation frequency of 500 Hz will have a 10× sampling rate. In accordance with at least one aspect of the invention, the modulation frequency will typically be selected to maximize sampling rate for incorporation events while maintaining a minimum sampling rate for non-incorporation events. As will be appreciated, where one wishes to provide such sampling rates using multiple excitation beams, the frequency of illumination for the collective excitation beams may be accordingly increased, e.g., 3× for 3 beams.

In contrast, where one wishes to minimize adverse effects of illumination, e.g., autofluorescence or other noise contributions, heating, photodamage or the like, one may wish to select a modulation frequency that provides a sampling rate that is sufficient that one can be confident that incorporation events are illuminated, but not to the point of causing damaging events to occur. In such cases, lower sampling rates may be desired, e.g., 1×, 2×, 3× or 4×. In the case of single molecule detection methods, described above, e.g., single molecule real time sequencing, residence times (and their consequent emission pulses in an illumination volume) can vary relatively dramatically, e.g., as set forth above. As such, modulation frequencies will typically be selected to provide the absolute minimum desired sampling, e.g., 1× or 2× for the shortest signal events, e.g., 10 ms or less. Accordingly, in preferred applications, modulation frequencies will typically be about 100 Hz or higher. In cases where higher sampling rates are desired or for shorter duration pulses, modulation frequencies of 200 Hz or greater, 500 Hz or greater, 1000 Hz or greater. In the case where only longer pulse durations are expected, slower frequency modulation may be employed, e.g., down to at least 20 Hz, at least 50 Hz or the like. In any event, modulation frequencies will typically fall between 20 Hz and 1000 Hz, with preferred frequencies falling between about 50 and about 500 Hz and still further preferred frequencies falling between about 100 and about 500 Hz. While the foregoing frequency ranges are preferred for applications in which, sampling rates and reaction times fit within the foregoing ranges, it will be appreciated that for longer or shorter reaction times, lower or higher frequency modulation may be used, respectively, to achieve a desired sampling rate.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A system for analysis of fluorescent materials, comprising:
    a reaction region for containing a fluorescent reaction mixture;
    at least first and second excitation light sources;
    at least one detector; and
    an optical train for directing excitation light from the at least first and second excitation light sources to the reaction region and collecting fluorescent signals from the reaction region and directing the fluorescent signals to the detector,
    wherein the optical train comprises a beam modulation component that modulates the excitation light from the at least first and second excitation light sources, the optical train is configured to provide at least first and second modulated beams of excitation light to the reaction region at different times, the optical beam modulation component is configured to modulate the excitation light at a frequency of between about 20 Hz and about 1000 Hz, and
    the detector is configured to detect each type of the fluorescent signals corresponding to each of the at least first and second modulated beams of the excitation light at different times, wherein the detector is synchronized with the at least first and second modulated beams of excitation light to have a sampling rate that is greater than the frequency of modulation of the at least first and second modulated beams, thus substantially reducing the background noise from reflected excitation lights and autofluorescence.

2. The system of claim 1, wherein the beam modulation component modulates an excitation beam from at least one of the at least first and second excitation light sources.

3. The system of claim 2, wherein the beam modulation component comprises a mechanical beam chopper.

4. The system of claim 2, wherein the beam modulation component comprises an acousto-optical modulator.

5. The system of claim 2, wherein the beam modulation component comprises a digital light processor.

6. The system of claim 1, wherein the beam modulation component is configured to modulate the excitation beam at a frequency of between about 100 Hz and about 500 Hz.

7. The system of claim 1, wherein the detector has the sampling rate that is greater than 1× the frequency of modulation.

8. The system of claim 1, wherein the detector has the sampling rate that is greater than 2× the frequency of modulation.

9. The system of claim 1, wherein the detector has the sampling rate that is greater than 4× the frequency of modulation.

10. The system of claim 1, wherein the detector has the sampling rate that is greater than 10× the frequency of modulation.

11. The system of claim 1, wherein the reaction region comprises an enzyme reagent and at least a first fluorescent reactant for the enzyme.

12. The system of claim 11, wherein the enzyme reagent comprises a nucleic acid polymerizing enzyme and the fluorescent reactant comprises at least a first fluorescent nucleotide analog.

13. The system of claim 12, wherein the fluorescent reactant comprises at least four different types of fluorescent nucleotide analogs.

14. The system of claim 12, wherein the polymerizing enzyme is immobilized upon a substrate in a single molecule configuration.

15. The system of claim 1, wherein the detector comprises a CCD camera.

16. A system for analysis of fluorescent materials, comprising:
    a reaction region containing a reaction mixture that comprises at least first and second fluorescent reactants, the first and second fluorescent reactants having at least first and second distinct excitation spectra;
    at least first and second excitation light sources configured to provide at least first and second excitation light beams at the at least first and second excitation spectra, respectively; and
    an optical train for modulating the at least first and second excitation light beams from the at least first and second excitation light sources at a frequency of at least 50 Hz to provide at least first and second modulated excitation light beams and for directing the at least first and second modulated excitation light beams to the reaction region at different times,
    wherein a detector is configured to detect each type of the fluorescent signals corresponding to each of the at least first and second modulated beams of the excitation light at different times,
    wherein the detector is synchronized with the at least first and second modulated beams of excitation light to have a sampling rate that is greater than the frequency of modulation of the at least first and second modulated beams, thus substantially reducing the background noise from reflected excitation lights and autofluorescence.

17. The system of claim 16, wherein the optical train modulates the at least first and second excitation light beams from the at least first and second excitation light sources, such that an excitation beam incident upon a substrate in the reaction region is substantially from only one of the at least first and second excitation light sources at a given time.

18. A method of detecting fluorescent reactants using the system of claim 1, comprising:
   providing the reaction mixture containing at least first and second fluorescent reactants;
   modulating the excitation light to provide the at least first and second modulated beams;
   directing the at least first and second modulated beams at the reaction region to excite the first and second fluorescent reactants, wherein simultaneous excitation of the first and second fluorescent reactants further excites at least one of the first and second fluorescent reactants to a triplet state; and
   detecting the fluorescent signals emitted from the at least first and second fluorescent reactants.

19. The method of claim 18, comprising directing the at least first and second modulated beams and a third modulated beam at the reaction region.

20. The method of claim 18, further comprising identifying a type of fluorescent signal produced by the reaction mixture based, at least in part, upon which of the first or second modulated beam was directed at the reaction region at a time that the fluorescent signal was produced.

* * * * *